US007574930B2

(12) United States Patent
Bunker

(10) Patent No.: US 7,574,930 B2

(45) Date of Patent: Aug. 18, 2009

(54) TRACE CHEMICAL SENSING

(75) Inventor: Stephen N. Bunker, Wakefield, MA (US)

(73) Assignee: Implant Sciences Corporation, Wilmington, MA (US)

(*) Notice: Subject to any disclaimer, the term of this patent is extended or adjusted under 35 U.S.C. 154(b) by 382 days.

(21) Appl. No.: 11/654,394

(22) Filed: Jan. 17, 2007

(65) Prior Publication Data

US 2007/0158447 A1 Jul. 12, 2007

Related U.S. Application Data

(63) Continuation-in-part of application No. 11/492,672, filed on Jul. 25, 2006, which is a continuation-in-part of application No. 11/258,477, filed on Oct. 25, 2005, and a continuation-in-part of application No. 10/890, 820, filed on Jul. 14, 2004, now Pat. No. 7,098,672, which is a continuation-in-part of application No. 10/349,491, filed on Jan. 22, 2003, now Pat. No. 6,828, 795, which is a continuation-in-part of application No. 10/295,039, filed on Nov. 14, 2002, now abandoned, and a continuation-in-part of application No. 10/295, 010, filed on Nov. 14, 2002, now Pat. No. 6,861,646, application No. 11/654,394, which is a continuation-in-part of application No. 11/248,603, filed on Oct. 12, 2005, which is a continuation-in-part of application No. 10/890,820, filed on Jul. 14, 2004, now Pat. No. 7,098,672, and a continuation-in-part of application No. 10/853,563, filed on May 25, 2004, now Pat. No. 7,244,288, said application No. 11/248,603 is a continuation-in-part of application No. 10/818,434, filed on Apr. 5, 2004, now Pat. No. 6,870,155, which is a continuation-in-part of application No. 10/754,088, filed on Jan. 7, 2004, now Pat. No. 6,888,128.

(60) Provisional application No. 60/708,017, filed on Aug. 12, 2005.

(51) Int. Cl.

| | |
|---|---|
| ***G01N 1/02*** | (2006.01) |
| ***G01N 1/08*** | (2006.01) |
| ***G01N 1/22*** | (2006.01) |
| ***G01N 1/40*** | (2006.01) |

(52) U.S. Cl. ............... 73/864.33; 73/863.21; 73/863.23

(58) Field of Classification Search ............. 73/863.21, 73/863.23, 864.33

See application file for complete search history.

(56) References Cited

U.S. PATENT DOCUMENTS 4,602,962 A * 7/1986 Fehlmann .................. 106/405

(Continued)

FOREIGN PATENT DOCUMENTS

JP 01151961 A * 6/1989

(Continued)

*Primary Examiner*—Thomas P Noland

(74) *Attorney, Agent, or Firm*—Muirhead and Saturnelli, LLC

(57) ABSTRACT

An explosive and narcotics detection system detects the presence of trace particles of materials that are adhering to surfaces. In order to detect such particles, to the particles are first dislodged or released from the surface, then transported to the detection instrument, and then accumulated on or in a particle collection device. When the sample collecting system and the target surface are in relative motion across the line-of-sight greater than fifteen centimeters per second, non-contact sample collection may be accomplished using a vortex or vortex attractor particle collector together with a plurality of air or aerosol jets. A plurality of large diameter vortex collectors may obtain samples at relative line-of-sight velocities greater than five feet per second over a large surface area and for a complex-shaped surface.

22 Claims, 6 Drawing Sheets

U.S. PATENT DOCUMENTS

| | | | | |
|---|---|---|---|---|
| 5,854,431 | A | 12/1998 | Linker et al. | 73/863.23 |
| 5,958,094 | A * | 9/1999 | Schwamborn et al. | 55/331 |
| 6,484,594 | B1 * | 11/2002 | Saaski et al. | 73/863.21 |
| 6,520,034 | B1 | 2/2003 | Masquelier et al. | 73/863.21 |
| 6,576,262 | B1 * | 6/2003 | Hanna et al. | 424/489 |
| 6,870,155 | B2 * | 3/2005 | Krasnobaev et al. | 250/283 |
| 7,261,008 | B2 * | 8/2007 | Saaski et al. | 73/863.22 |
| 7,390,339 | B1 * | 6/2008 | Warrick et al. | 55/346 |
| 7,405,073 | B2 * | 7/2008 | Tilles et al. | 435/287.1 |
| 2003/0155506 | A1 | 8/2003 | Motchkine et al. | 250/288 |
| 2004/0063197 | A1 * | 4/2004 | Tilles et al. | 435/287.2 |

FOREIGN PATENT DOCUMENTS

| | | | |
|---|---|---|---|
| JP | 2001289769 | A * | 10/2001 |
| WO | WO 00/16064 | | 3/2000 |
| WO | WO 01/33084 | A1 | 5/2001 |

* cited by examiner 300
305
311
309
304
303
309
310
350
308
353
307
306
355
302
301

TRACE CHEMICAL SENSING

CROSS-REFERENCE TO RELATED APPLICATIONS

This application is a Continuation-in-part of U.S. application Ser. No. 11/492,672, filed Jul. 25, 2006 (pending), which is a Continuation-in-part of U.S. Ser. No. 11/258,477, filed Oct. 25, 2005 (pending), and which claims priority to Provisional Application 60/708,017, filed Aug. 12, 2005 (expired), and which is a Continuation-in-part of U.S. Ser. No. 10/890,820, filed Jul. 14, 2004 (now U.S. Pat. No. 7,098,672), which is a Continuation-in-part of U.S. Ser. No. 10/349,491, filed Jan. 22, 2003 (now U.S. Pat. No. 6,828,795), which is a Continuation-in-part of U.S. Ser. No. 10/295,039, filed Nov. 14, 2002 (abandoned), and which is a Continuation-in-part of U.S. Ser. No. 10/295,010, filed Nov. 14, 2002 (now U.S. Pat. No. 6,861,646), which claims priority from Provisional Application 60/363,485, filed Mar. 12, 2002 (expired), and Provisional Application 60/357,618, filed Feb. 15, 2002 (expired), and Provisional Application 60/357,394, filed Feb. 15, 2002 (expired), all of which are incorporated herein by reference.

This application is also a Continuation-in-part of U.S. application Ser. No. 11/248,603, filed Oct. 12, 2005 (pending), which is a Continuation-in-part of U.S. Ser. No. 10/890,820, filed Jul. 14, 2004 (now U.S. Pat. No. 7,098,672), and which is a Continuation-in-part of U.S. Ser. No. 10/853,563, filed May 25, 2004, (now U.S. Pat. No. 7,244,288), and which claims the benefit of Provisional Application 60/473,649, filed May 28, 2003. U.S. application Ser. No. 11/248,603 is also is a Continuation-in-part of U.S. Ser. No. 10/818,434, filed Apr. 5, 2004 (now U.S. Pat. No. 6,870,155), which is a Continuation-in-part of U.S. Ser. No. 10/754,088, filed Jan. 7, 2004 (now U.S. Pat. No. 6,888,128), which claims priority from Provisional Application 60/363,485, filed Mar. 12, 2002 (expired), and Provisional Application 60/357,394, filed Feb. 15, 2002 (expired), and Provisional Application 60/357,618, filed Feb. 15, 2002 (expired), all of which are incorporated herein by reference.

BACKGROUND OF THE INVENTION

1. Field of the Invention

This application relates to detection of chemical traces of substances such as explosives or narcotics and, more particularly, to the non-contact collection of particles of the substances from a surface that is moving with relative motion to a trace sample collection system.

2. Description of Related Art

There exist a wide variety of instruments that are capable of detecting and identifying particles of narcotics or explosives once the sample of particles is transported to the instrument and subsequently vaporized. Examples include, but are not limited to, ion mobility spectrometers, mass spectrometers, gas chromatographs, surface acoustic wave sensors, cantilever beam sensors, and electron capture detectors. Similarly, there are several ways commonly employed to transport said particles to the instrument, some of which are incorporated within the instrument and some requiring an operator to perform the transfer. Examples include, but are not limited to, mechanically transporting a collected sample to the instrument, vacuum collection of vapor or particles, and vortex vacuum sampling.

In the above examples, the particles begin by being attached to a surface by weak chemical bonds, van der Waals forces, mechanical attachment in a fibrous structure or porosity, electrostatic attraction, or entrainment in a sticky material, such as grease. For narcotics and explosives particles, the surface adhesion forces can be relatively strong, making the particles difficult to remove by simple, low momentum transfer methods, such as blowing a puff of air. Removal of such strongly adhered particles by blowing air is usually successful only for the largest, heaviest particles that present the greatest surface area to the blowing air. In general, blowing air does not readily remove particles of explosives or narcotics from rigid surfaces, only from flexible surfaces, such as cloth, where the fluttering motion of the material provides the momentum to mechanically dislodge the particles, or from unstable surfaces, such as cardboard, where the substrate material can flake off together with the target particle. Even with cloth, the blowing air stream usually requires a very high velocity flow to have any effect and then only for the largest particles, so the process is very inefficient. Surfaces subject to blowing air during normal usage, such as the sides of a vehicle, are particularly difficult for obtaining a trace chemical sample simply by employing an air jet.

The distance between the target surface and the blowing air jet is also relevant. Air jets from nozzles are known to diverge and slow in velocity with distance traversed due to interaction with the surrounding atmosphere, making them lose efficiency for particle removal with increasing standoff distance. A nozzle that employs an aerosol that includes pressurized gas and solid particles in order to enhance target particle release is similarly affected, and the aerosol particles slow rapidly with standoff distance.

In some cases, the process of taking a sample begins with an operator or a machine physically wiping an absorbent, often textured substance, such as chemical filter paper, onto the surface to be tested. Particles of the chemical of interest may then be transferred and concentrated on or in the surface texture of the absorber by the mechanical action of the wiping. This intermediate absorber is then brought to the vicinity of the detection instrument to make a measurement. The wiping method generally works reliably and efficiently but can be costly, because the media usually has to be replaced often.

There are many applications in which it is desirable to avoid having to manually wipe a surface to obtain trace particles. These include sampling without an operator, large area sampling, remote sampling, robotic sampling, and situations in which the frequent replacement of wiping materials is not acceptable. Examples of applications desirable for non-contact sample acquisition include the examination of people, packages, baggage, mail, objects on a manufacturing production line, and vehicles. However, the targets of each of these applications are often in motion, for example, items on a moving belt, walking persons, and moving vehicles. While it is possible to require that these targets stop moving during the sensing process, it would be preferable to examine these targets while they are in motion relative to the trace sample collection system. It would also be preferable for a trace sample collection system to operate with similar efficiency whether it is the target object that is moving with a static trace sample collection system or the trace sample collection system is moving with a static target object. In some cases, both target object and trace sample collection system may preferably be in motion. Examples in which the sample acquisition system is in motion with a static target object include a robot scanning along the side of a suspect vehicle, and a human explosives detection portal in which the sample acquisition system scans along the side of a person.

Accordingly, it would be desirable to provide a trace sample collection system that allows for the efficient collection of a target particle sample while the target surface and the trace sample collection system are in relative motion.

SUMMARY OF THE INVENTION

According to the system described herein, a method for non-contact collection of trace particles of explosives or narcotics from a target surface includes releasing the trace particles from the target surface. The transport that is provided for the trace particles includes a vortex directed outwardly towards the target surface, wherein the vortex projects from an exit orifice for an outwardly blowing and spinning gas flow that is concentric with an inwardly flowing gas and air flow. The trace particles are collected from said inwardly flowing gas and air flow, wherein a relative velocity across the line-of-sight between said target surface and the exit orifice for said outwardly blowing and spinning gas flow is greater than fifteen centimeters per second.

According further to the system described herein, a trace sample collection system is provided for the purpose of collecting a target particle sample while the target surface and the trace sample collection system are in relative motion. Relative motion is defined as a relative velocity across the line-of-sight between the target surface and the trace sample collection system, and may be greater than fifteen centimeters (six inches) per second. For example, objects moving on a belt often may be moving at a speed greater than fifteen centimeters (six inches) per second, and speeds up to sixty centimeters (two feet) per second are common. A walking person may be moving at a speed between sixty and one hundred centimeters (two to three feet) per second. Moving vehicles can be much faster.

According further to the system described herein, a system for non-contact collection of trace particles of explosives or narcotics from a target surface includes a particle release component, a particle transport component, and a particle collection component. The particle release component releases the trace particles from the target surface. The particle transport component transports the trace particles from the target surface, wherein the particle transport component provides a vortex directed outwardly towards the target surface, wherein the vortex projects from an exit orifice for an outwardly blowing and spinning gas flow that is concentric with an inwardly flowing gas and air flow. The particle collection component that collects the trace particles from the inwardly flowing gas and air flow, wherein a relative velocity across the line-of-sight between the target surface and the exit orifice for the outwardly blowing and spinning gas flow is greater than fifteen centimeters per second.

According further to the system described herein, the particle release component may include a nozzle for a gas jet or an aerosol jet, either of which may be provided with a source of pressurized gas and directed towards a target surface that may be contaminated with traces of narcotics or explosives related chemicals. The source of pressurized gas may be operated continuously or preferably be pulsed. A pulse may be preferably less than one second. The pressure of the pressurized gas may be about one hundred pounds per square inch, a value easily obtained with small compressors, but significantly higher pressures may also be employed, and may be limited only by the availability, cost, and safety restrictions for the pressurized gas. For example, a high pressure tank of gas may not be acceptable in a public area due to the risk of explosion caused by mishandling.

According further to the system described herein, jets of gas or jets of an aerosol mixture of particles and gas are employed to assist in the release of target particles. The jets may be aimed to blow tangentially across a surface of the target object and towards the active zone of the particle transport component or the jets may be aimed to blow at a point on the target object that is within the active zone of the particle transport component.

According further to the system described herein, the particle transport component may be a vortex sampling system, a version of which is sometimes referred to as a vortex attractor. The vortex sampling system may include an outwardly blowing and spinning gas stream operating in concert with an inwardly flowing gas and air stream that entrains and transports the target chemical sample particles. The outwardly blowing and spinning gas stream of the sample acquisition system may surround the inwardly flowing gas and air stream and spin about the axis defined by the inwardly flowing gas and air stream.

According further to the system described herein, the partial vacuum formed by the inwardly flowing gas and air stream may be of sufficient strength to provide a force radially inwards towards the axis defined by the inwardly flowing gas and air stream that is substantially equal to the radially outwards centrifugal force of the outwardly blowing and spinning gas stream.

According further to the system described herein, the outwardly blowing and spinning gas stream may be provided by at least one of a gas pump, a fan, an impeller, a blower, an air knife, or a pressurized air supply. The inwardly flowing gas and air stream may be induced by at least one of a vacuum pump, a fan, an impeller, or a Venturi vacuum generator.

According further to the system described herein, the gas of the blowing and spinning gas stream may be at least one of air, nitrogen, carbon dioxide, or argon. The gas of the blowing and spinning gas stream may be heated above ambient temperature. Further, the gas of the blowing and spinning gas stream may contain additive chemicals to enhance the detection performance of the sample collection system.

According further to the system described herein, the source for the intake for the mechanism for inducing the outwardly blowing and spinning gas stream may also substantially provide the inward flowing gas and air stream. In this case, the vortex sampling system may be defined as a vortex attractor.

According further to the system described herein, the maximum relative velocity across the line-of-sight between the exit orifice for the outwardly blowing and spinning gas and the target surface may be proportional to the diameter of the exit orifice and is approximately four times the diameter per second. Since the relative velocity across the line-of-sight is defined as at least fifteen centimeters per second, the exit orifice of the blowing and spinning gas would need to be at least 3.7 centimeters (1.5 inches) in diameter. The useful maximum working distance from the exit orifice for the efficient collection of target particles is approximately one to two times the diameter of the exit orifice or about 3.7 to 7.5 centimeters (1.5 to 3 inches) for a 3.7 centimeter diameter. Similarly, a vortex with an exit orifice of 1.3 feet could accept a maximum relative velocity of 5.3 feet per second at a distance up to 2.6 feet.

According further to the system described herein, the zone on the target surface from which target particles may be directly collected may be determined by the area where the inward flowing gas and air intersects the surface of the target object while the target object or trace sample collection system move during the sampling period. The diameter of the inward flowing gas and air may be approximately eighty percent of the diameter of the exit orifice of the blowing and spinning air. For a surface whose normal axis is parallel to the axis of the trace sample collection system and moving perpendicular to the trace sample collection system, the area may be a "racetrack" shape with semicircular ends having a diameter of the inward flowing gas and air and a central rectangular zone with one side the same as the semicircular end diameter and the other side the speed between the target surface and the trace sample collection system times the sampling period. For example, if the target object is moving perpendicular to the trace sample collection system at two feet per second, sampling lasts for two seconds, and the exit orifice diameter is 1.33 feet, the stripe on the target object from which target particles may be directly collected is 1.06 feet by 5.06 feet with semicircular ends. Therefore, it may be preferable that the exit orifice be as large as possible for the application to maximize the area of the target surface that can be sampled with a single trace sample collection system.

According further to the system described herein, a plurality of trace sample collection systems may be employed in order to increase the sampled area of target surface as well as decrease the time required to obtain said sample. An example of the use of a plurality of trace sample collection systems would be at least one vertical array of trace sample collection systems disposed to one or both sides of a walking person, said arrangement referred to as a turnstile. Another example would be at least two sample collecting systems disposed at the sides of a moving belt carrying packages or baggage. At least one other trace sample collection system could be optionally disposed over the moving belt. Additionally, additional trace sample collecting systems may be optionally added for the purposed of permitting an increase of the belt speed by alternating which of the trace sample collecting systems is currently sampling and which is currently analyzing a sample previously collected.

According further to the system described herein, the particle collection component may be any of a variety of particle collecting techniques. Examples include, but are not limited to, a mesh filter, a woven three dimensional mesh, a filter made of commonly employed filter materials, an absorbent surface that may be chemically coated to enhance adhesion, a vortex particle separator, an electrostatic particle collector, a particle impactor, and an engineered material with finely etched openings to pass air but retain particles.

BRIEF DESCRIPTION OF THE DRAWINGS

Embodiments of the system are described with reference to the several figures of the drawings, in which.

DETAILED DESCRIPTION OF VARIOUS EMBODIMENTS

Figure 1:
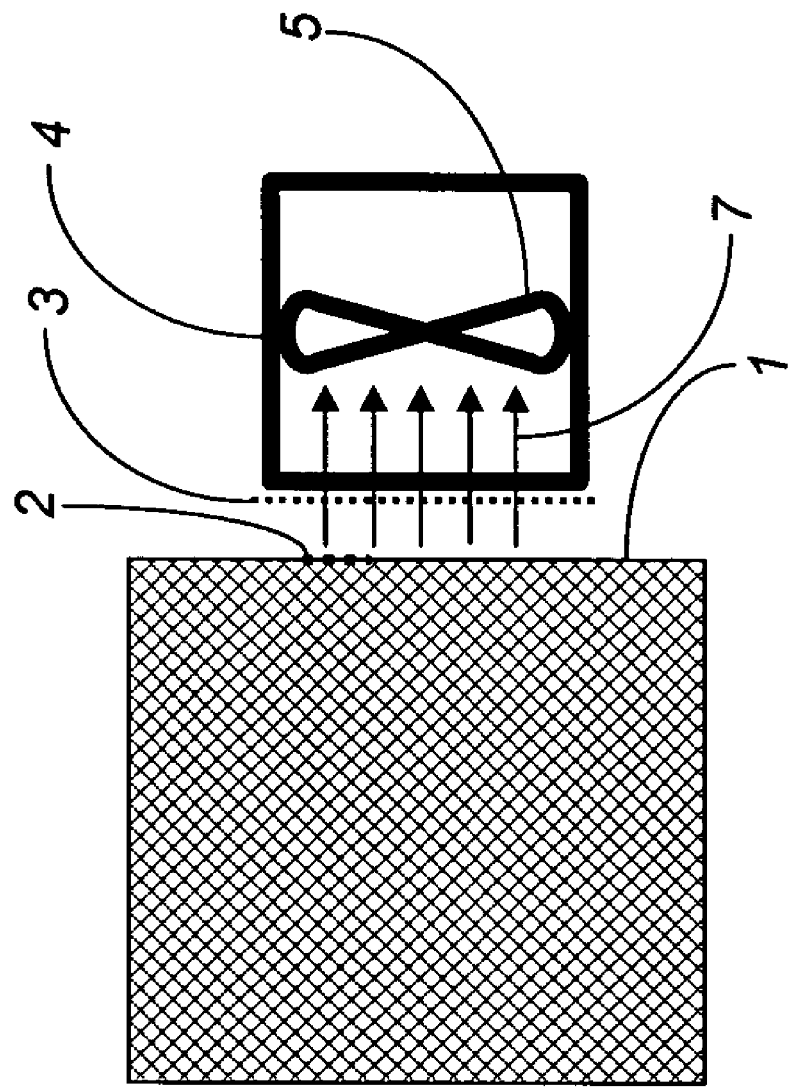
FIG. 1 is a schematic diagram of a handheld vacuum with a trace particle collection filter used in conjunction with existing wiping systems.

A handheld vacuum with a trace particle collection filter used in conjunction with existing wiping systems is illustrated in FIG. 1 showing basic features of non-contact particle collection system based on the existing state-of-the-art. The sample collection device 4 is brought in very close proximity to a target surface 1 that may have a trace sample of target particles 2. The vacuum pump 5 of the sample collection device 4 is activated, creating an inward flow of air 7. Sample collecting media 3 is disposed between the target surface 1 and the vacuum pump 5 such that any trace particles may be collected on or in the sample collecting media 3. The sample collecting media 3 may be a filter, such as chemical filter paper. The sample collecting media 3 is then removed from the sample collection device 4 and transported to a separate detection instrument in order to determine if trace particles of the target substance were collected. The separation distance between the sample collection device 4 and the target surface is typically less than an inch and often much less than an inch, because the vacuum pump 5 is usually battery operated for portability and does not produce much air flow through the sample collecting media 3. The sample collection device 4 may also rub on the target surface 1 in order to mechanically abrade trace particles and improve efficiency for collection. However, when used in that mode, it is not a non-contact sample collection system.

Figure 2:
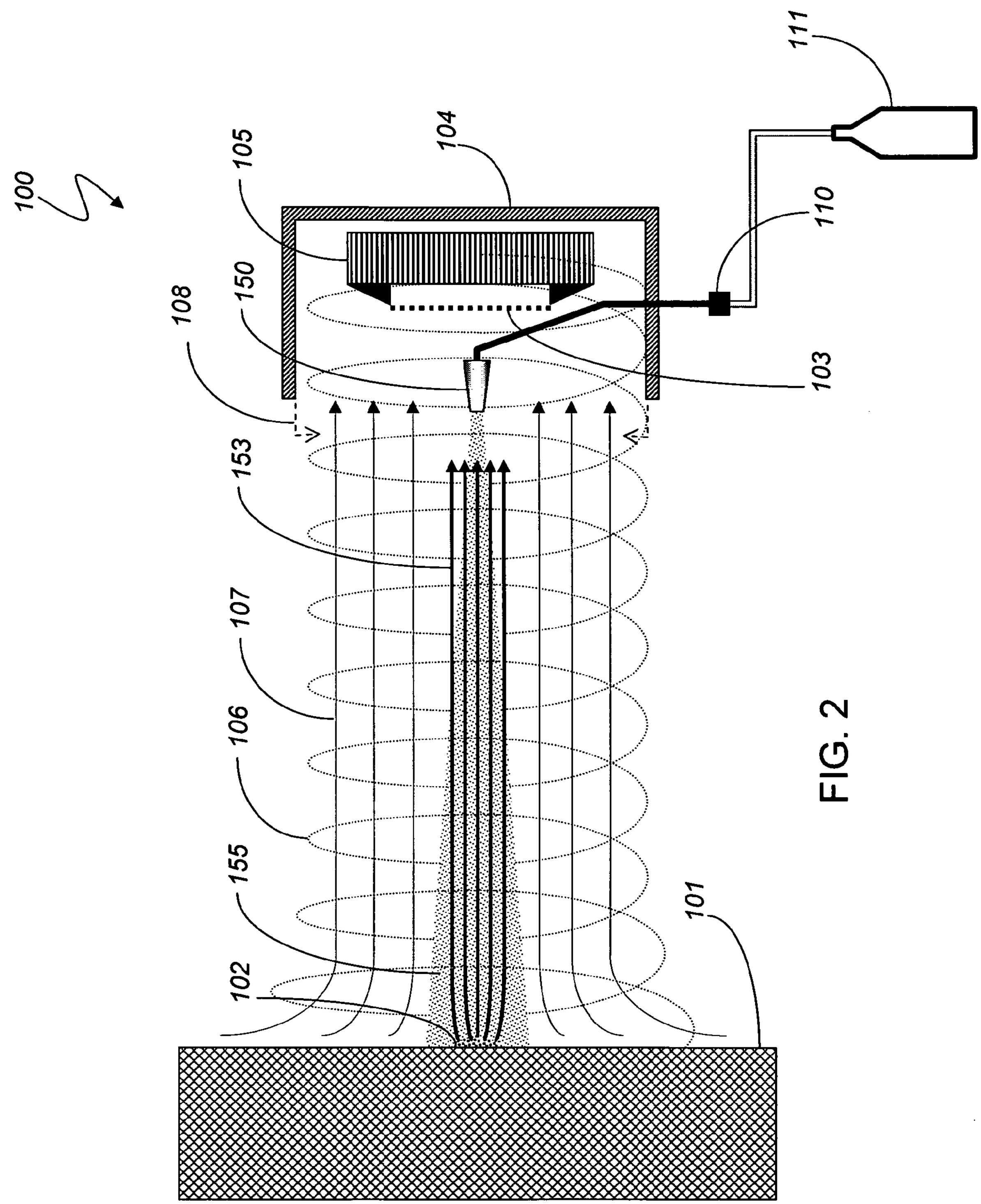
FIG. 2 is a schematic diagram showing a particle release system and method of operation in which a jet nozzle is disposed within the gas and air flow that is inwardly flowing towards the trace sample collection system, which is in the form of a vortex attractor, according to an embodiment of the system described herein.

FIG. 2 shows a system 100 for trace particle release, transport and collection and a method of operation according to an embodiment of the system described herein. A particle release component may include a jet nozzle 150 that may be disposed within a gas and air flow 107 that is inwardly flowing towards the trace sample collection system 104, and which may be in the form of a vortex attractor. An outwardly blowing and spinning gas flow 106 may be emitted from an exit orifice 108. The vortex attractor may use a single mechanism for producing both the outwardly blowing and spinning gas flow 106 and the inwardly flowing gas and air flow 107, which is here shown as an impeller fan 105. The nozzle 150 may be provided with gas from a reservoir 111, and the gas flow may be turned on and off using a control valve 110, which may be optionally activated electrically. The nozzle 150 may be disposed within the zone of the trace sample collection system 104 wherein the gas and air flow 107 is inwardly flowing, as indicated by the direction of the arrows. The output of the nozzle 150 may be a jet of gas 155 that impacts target surface 101 in order to release trace particles of explosives or narcotics 153 from a spot 102 on a target surface 101. Sample collecting media 103 may be disposed within the inwardly flowing gas and air flow 107, which may also entrain the released trace particles of explosives or narcotics 153. The sample collecting media 103 may be stainless steel mesh which may provide ease of cleaning and longevity.

The system 100 may provide for non-contact collection of a target particle sample while the target surface 101 and the trace sample collection system 104 are in relative motion, as further described elsewhere herein. Relative motion may be defined as a relative velocity across the line-of-sight between the target surface and the trace sample collection system, and may be greater than fifteen centimeters (six inches) per second. For example, objects moving on a belt often may be moving at a speed greater than fifteen centimeters (six inches) per second, and speeds up to sixty centimeters (two feet) per second are common. A walking person may be moving at a speed between sixty and one hundred centimeters (two to three feet) per second. Moving vehicles can be much faster.

The nozzle 150 of the particle release component may emit a gas jet or an aerosol jet, either of which may be provided with a source of pressurized gas (reservoir 111) and directed towards the target surface 101 that may be contaminated with traces of narcotics or explosives related chemicals. The source of pressurized gas may be operated continuously or preferably be pulsed. A pulse may be preferably less than one second. The pressure of the pressurized gas may be about one hundred pounds per square inch, a value easily obtained with small compressors, but significantly higher pressures may also be employed, and may be limited only by the availability, cost, and safety restrictions for the pressurized gas. For example, a high pressure tank of gas may not be acceptable in a public area due to the risk of explosion caused by mishandling.

The particle transport component may include a vortex sampling system, a version of which is sometimes referred to as a vortex attractor, and may use a mechanism such as the impeller fan 105. The vortex sampling system may include the outwardly blowing and spinning gas stream 106 operating in concert with an inwardly flowing gas and air stream 107 that entrains and transports the target chemical sample particles. The outwardly blowing and spinning gas stream 106 of the sample acquisition system may surround the inwardly flowing gas and air stream 107 and spin about the axis defined by the inwardly flowing gas and air stream 107.

The jets of gas or jets of an aerosol mixture of particles and gas from the nozzle 150 may be employed to assist in the release of target particles. The jets may be aimed to blow tangentially across a surface of the target object 101 and towards the active zone of the particle transport component or the jets may be aimed to blow at a point on the target object that is within the active zone of the particle transport component, as further described elsewhere herein.

A partial vacuum may be formed by the inwardly flowing gas and air stream 107 that may be of sufficient strength to provide a force radially inwards towards the axis defined by the inwardly flowing gas and air stream 107 that is substantially equal to the radially outwards centrifugal force of the outwardly blowing and spinning gas stream 106. In various embodiments, the outwardly blowing and spinning gas stream 106 may be provided by at least one of a gas pump, a fan, an impeller, a blower, an air knife, or a pressurized air supply, and the inwardly flowing gas and air stream 107 may be induced by at least one of a vacuum pump, a fan, an impeller, or a Venturi vacuum generator. The gas of the outwardly blowing and spinning gas stream 106 may be at least one of air, nitrogen, carbon dioxide, or argon, may be heated above ambient temperature, and may contain additive chemicals to enhance the detection performance of the sample collection system 104. The source for the intake for the mechanism for inducing the outwardly blowing and spinning gas stream 106 may also substantially provide the inward flowing gas and air stream 107. In this case, as further described elsewhere herein, the vortex sampling system may be defined as a vortex attractor.

The maximum relative velocity across the line-of-sight between the exit orifice 108 for the outwardly blowing and spinning gas flow 106 and the target surface 101 may be proportional to the diameter of the exit orifice 108 and may be approximately four times the diameter per second. Since the relative velocity may be at least fifteen centimeters per second, an appropriate size for the exit orifice 108 of the outwardly blowing and spinning gas 106 may be at least 3.7 centimeters (1.5 inches) in diameter. The useful maximum working distance from the exit orifice 108 for the efficient collection of target particles may be approximately one to two times the diameter of the exit orifice 108 or about 3.7 to 7.5 centimeters (1.5 to 3 inches) for a 3.7 centimeter diameter. Similarly, a vortex with an exit orifice 108 of 1.3 feet may accept a maximum relative velocity of 5.3 feet per second at a distance up to 2.6 feet. It is recognized that these values are based on typically encountered pumps and fans. A special high flow fan or pump may be capable of a greater maximum working distance and greater relative velocity.

The zone on the target surface 101 from which target particles may be directly collected is determined by the area where the inward flowing gas and air 107 intersects the surface 101 of the target object while the target object or trace sample collection system 104 move during the sampling period. The diameter of the inwardly flowing gas and air flow 107 may be approximately eighty percent of the diameter of the exit orifice 108 of the outwardly blowing and spinning air flow 106. For a surface whose normal axis is parallel to the axis of the trace sample collection system 104 and moving perpendicular to the trace sample collection system 104, the sampled area may be a “racetrack” shape with semicircular ends having a diameter of the inward flowing gas and air flow 107 and a central rectangular zone with one side the same as the semicircular end diameter and the other side the relative speed between the target surface 101 and the trace sample collection system 104 times the sampling period. For example, if the target object is moving perpendicular to the trace sample collection system at two feet per second, sampling lasts for two seconds, and the exit orifice 108 diameter is 1.33 feet, the stripe on the target object from which target particles may be directly collected is 1.06 feet by 5.06 feet with semicircular ends. Therefore, it may be preferable that the exit orifice 108 be as large as possible for the application to maximize the area of the target surface 101 that can be sampled with a single trace sample collection system 104.

A plurality of trace sample collection systems may be employed in order to increase the sampled area of target surface as well as decrease the time required to obtain said sample, as further described elsewhere herein. An example of the use of a plurality of trace sample collection systems would be at least one vertical array of trace sample collection systems disposed to one or both sides of a walking person, said arrangement referred to as a turnstile. Another example would be at least two sample collecting systems disposed at the sides of a moving belt carrying packages or baggage. At least one other trace sample collection system may be optionally disposed over the moving belt. Additionally, additional trace sample collecting systems may be optionally added for the purpose of permitting an increase of the belt speed by alternating which of the trace sample collecting systems is currently sampling and which is currently analyzing a sample previously collected.

The trace sample collection system 104 may include components of any of a variety of particle collecting techniques. Examples include, but are not limited to, a mesh filter, a woven three dimensional mesh, a filter made of filter materials, an absorbent surface that may be chemically coated to enhance adhesion, a vortex particle separator, an electrostatic particle collector, a particle impactor, and an engineered material with finely etched openings to pass air but retain particles.

Figure 3:
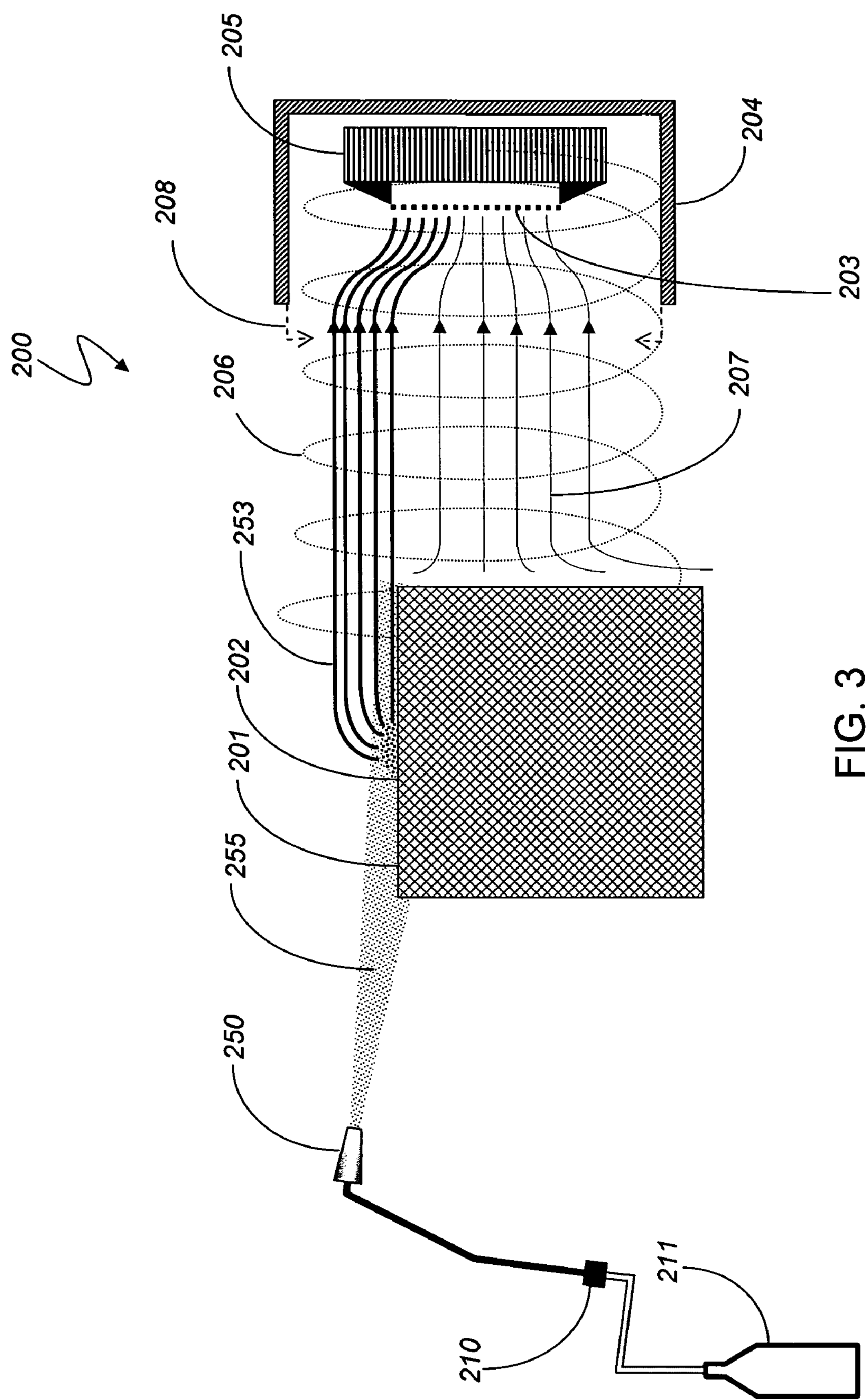
FIG. 3 is a schematic diagram showing a particle release system and method of operation in which a jet nozzle is aimed tangential to the target surface and towards the gas and air flow that is inwardly flowing towards the trace sample collection system, which is in the form of a vortex attractor, according to an embodiment of the system described herein.

FIG. 3 shows a system 200 for trace particle release, transport and collection and a method of operation according to another embodiment of the system described herein. A particle release component may include a jet nozzle 250 that may be disposed to aim tangentially to a target surface 201 and towards an inwardly flowing gas and air flow 207 of a trace sample collection system 204, which here is in the form of a vortex attractor. An outwardly blowing and spinning gas flow 206 may be emitted from an exit orifice 208. The vortex attractor may use a single mechanism for producing both the outwardly blowing and spinning gas flow 206 and the inwardly flowing gas and air flow 207, which is here shown as impeller fan 205. The nozzle 250 may be provided with gas from a reservoir 211, and the gas flow is turned on and off using a control valve 210, which may be optionally activated electrically. The output of the nozzle 250 may be a jet of gas 255 that impacts the target surface 201 in order to release trace particles of explosives or narcotics 253 from a spot 202 on the target surface 201. Optionally, the output of the nozzle 250 may be an aerosol of solid particles and gas. Sample collecting media 203 may be disposed within the inwardly flowing gas and air flow 207, which may also entrain the released trace particles of explosives or narcotics 253. The sample collecting media 203 may be stainless steel mesh which may provide ease of cleaning and longevity.

Figure 4:
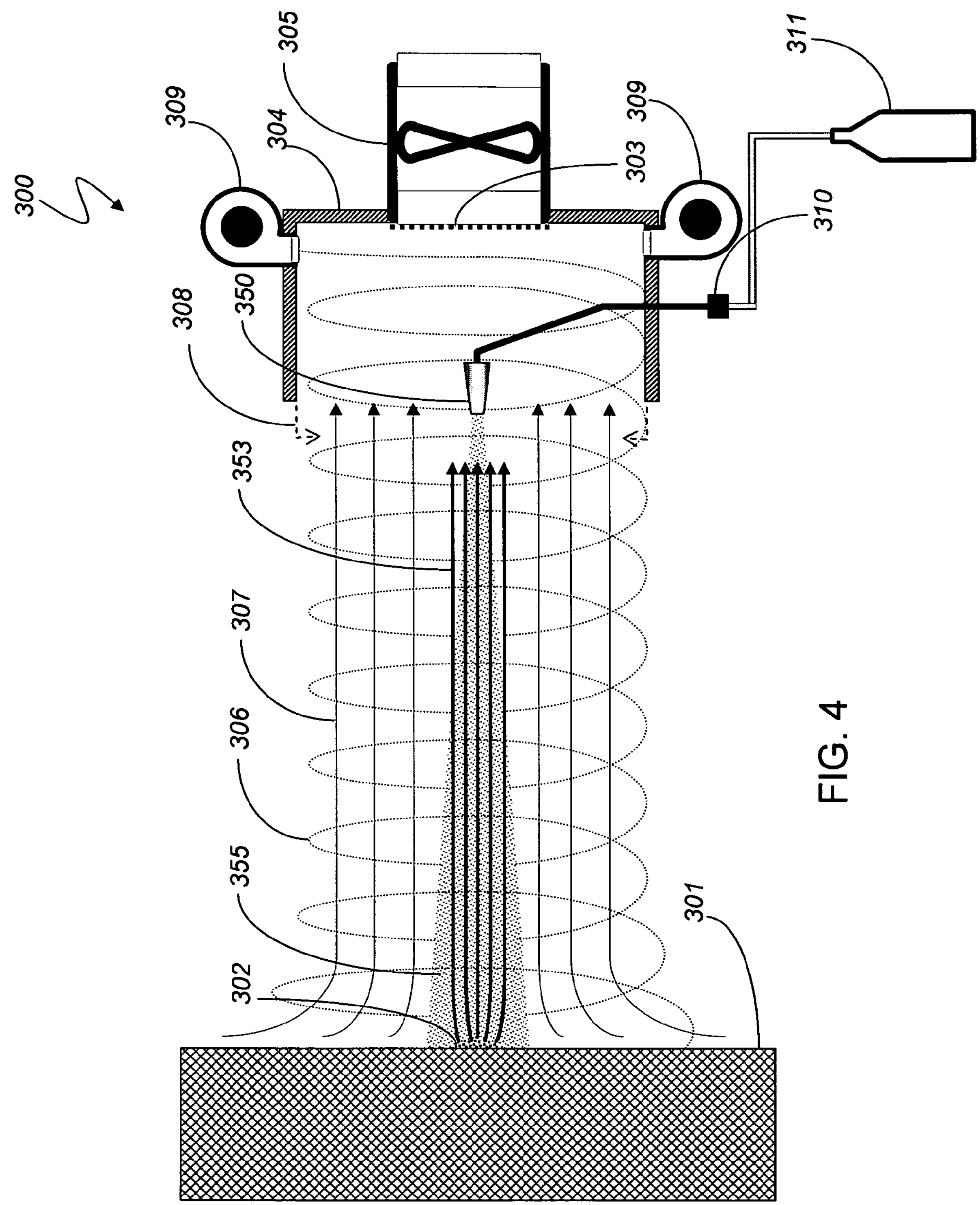
FIG. 4 is a schematic diagram showing a particle release system and method of operation in which a jet nozzle is disposed within the gas and air flow that is inwardly flowing towards the trace sample collection system, which is in the form of a vortex, according to an embodiment of the system described herein.

FIG. 4 shows a system 300 for trace particle release, transport and collection and a method of operation according to another embodiment of the system described herein. A particle release component may include a jet nozzle 350 that may be disposed within a gas and air flow 307 that is inwardly flowing towards a trace sample collection system 304, which is in the form of a vortex. An outwardly blowing and spinning gas flow 306 may be emitted from an exit orifice 308. The vortex may use separate mechanisms for producing the outwardly blowing and spinning gas flow 306 and the inwardly flowing gas and air flow 307, which are here shown as tangentially mounted blowers 309 and an axially mounted fan 305, respectively. The nozzle 350 may be provided with gas from a reservoir 311, and the gas flow may be turned on and off using a control valve 310, which may be optionally activated electrically. The nozzle 350 may be disposed within the zone of the trace sample collection system 304 wherein the gas and air flow 307 is inwardly flowing, as indicated by the direction of the arrows. The output of the nozzle 350 may be a jet of gas 355 that impacts the target surface 301 in order to release trace particles of explosives or narcotics 353 from a spot 302 on the target surface 301. Optionally, the output of the nozzle 350 may be an aerosol of solid particles and gas. Sample collecting media 303 may be disposed within the inwardly flowing gas and air flow 307 which may also entrain the released trace particles of explosives or narcotics 353.

Figure 5:
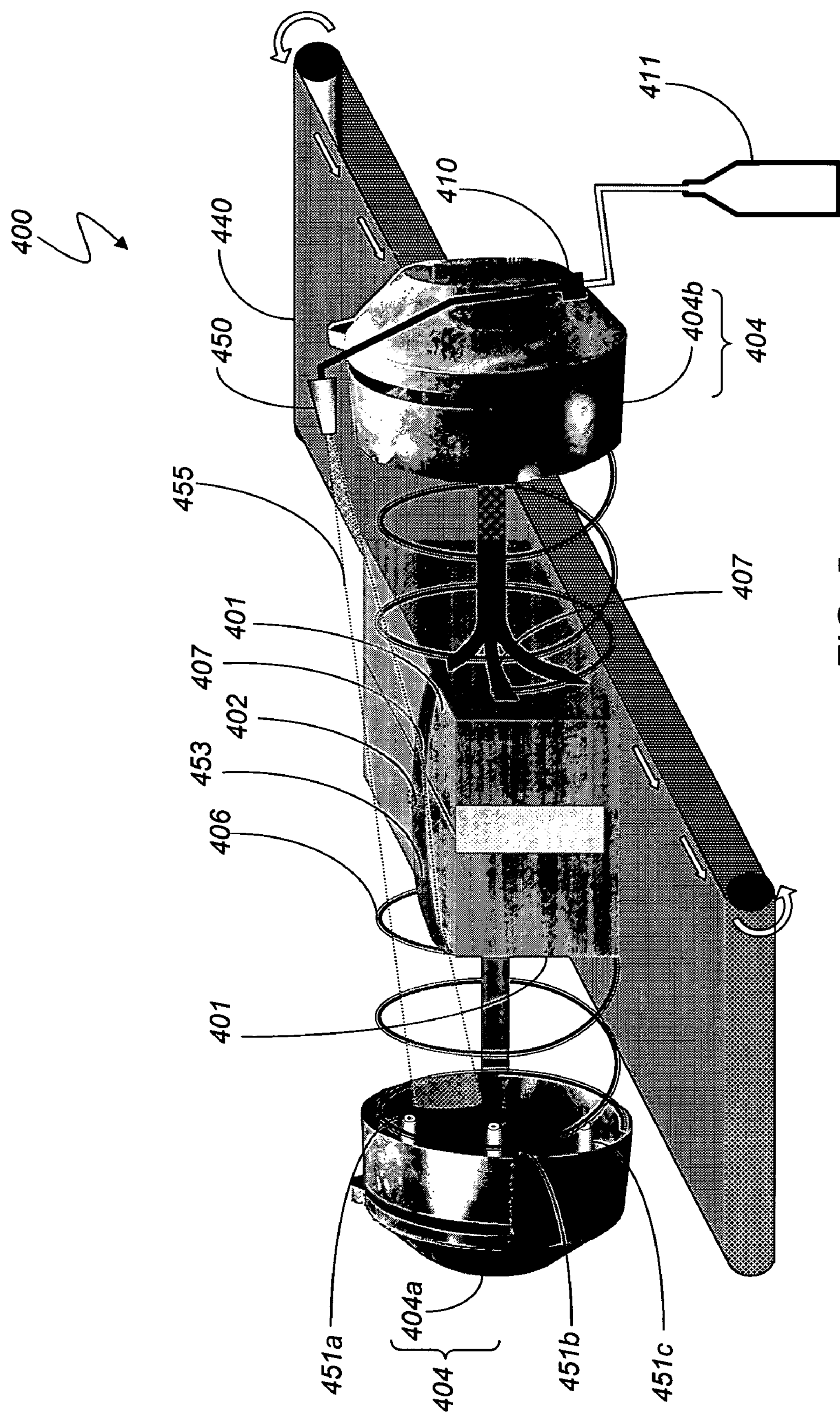
FIG. 5 is a schematic diagram showing an application of the method for non-contact collection of trace particles of explosives or narcotics from a target surface when the target object is moving on a belt and the trace sample collection system is static, according to an embodiment of the system described herein.

FIG. 5 shows a system 400 having a configuration that employs a method for the non-contact collection of trace particles of explosives or narcotics from a target surface according to an embodiment of the system described herein. In the illustrated configuration, a target object surface 401 is moving and a trace sample collection system 404 is static. The example shown is for a package on a moving belt 440, but a similar configuration may be used for baggage and objects on a production line. The trace sample collection system 404 may include two trace sample collection devices 404*a*, 404*b* based on a vortex attractor design and which are shown disposed to the sides of the moving belt 440 and facing towards the belt 440. The vortex attractor may use a single common mechanism, preferably an impeller, for producing both an outwardly blowing and spinning gas flow 406 and an inwardly flowing gas and air flow 407. Possible target surfaces 401 include the front and rear faces, the top face, and the two side faces of the package. In the example shown in the figure, particles 453 are being released from a particle source 402 on the top face. The nozzle 450 blows a jet 455 tangentially towards the target surface 401 and also aimed towards the zone of inwardly flowing gas and air 407 that is being produced by the trace sample collection system 404. Released particles 453 may be entrained in the gas flow of either or both of the trace sample collection devices 404*a,b*. The two trace sample collection devices 404*a,b* may be employed in the trace sample collection system 404 in order to be able to collect particles from multiple sides of three dimensional objects, such as a package. Two trace sample collection devices 404*a,b* may also be useful to balance the suction forces on the target object 401 that are produced by the inwardly flowing gas and air 407 in order to avoid moving lightweight objects. The two trace sample collection systems 404 may be further useful to increase overall detection efficiency and throughput speed. As an example of suction forces, if a single vortex attractor used as a trace sample collection system is disposed directly over the moving belt, there is a risk of lifting lightweight packages, such as large shipping envelopes, up off the belt towards the vortex attractor. The system shown in this example may also include other nozzles 451*a*, 451*b*, 451*c* that are disposed within the inwardly flowing gas and air 407. The nozzles 451*a-c* may preferably be used for releasing trace particles from the side faces of the package.

Figure 6:
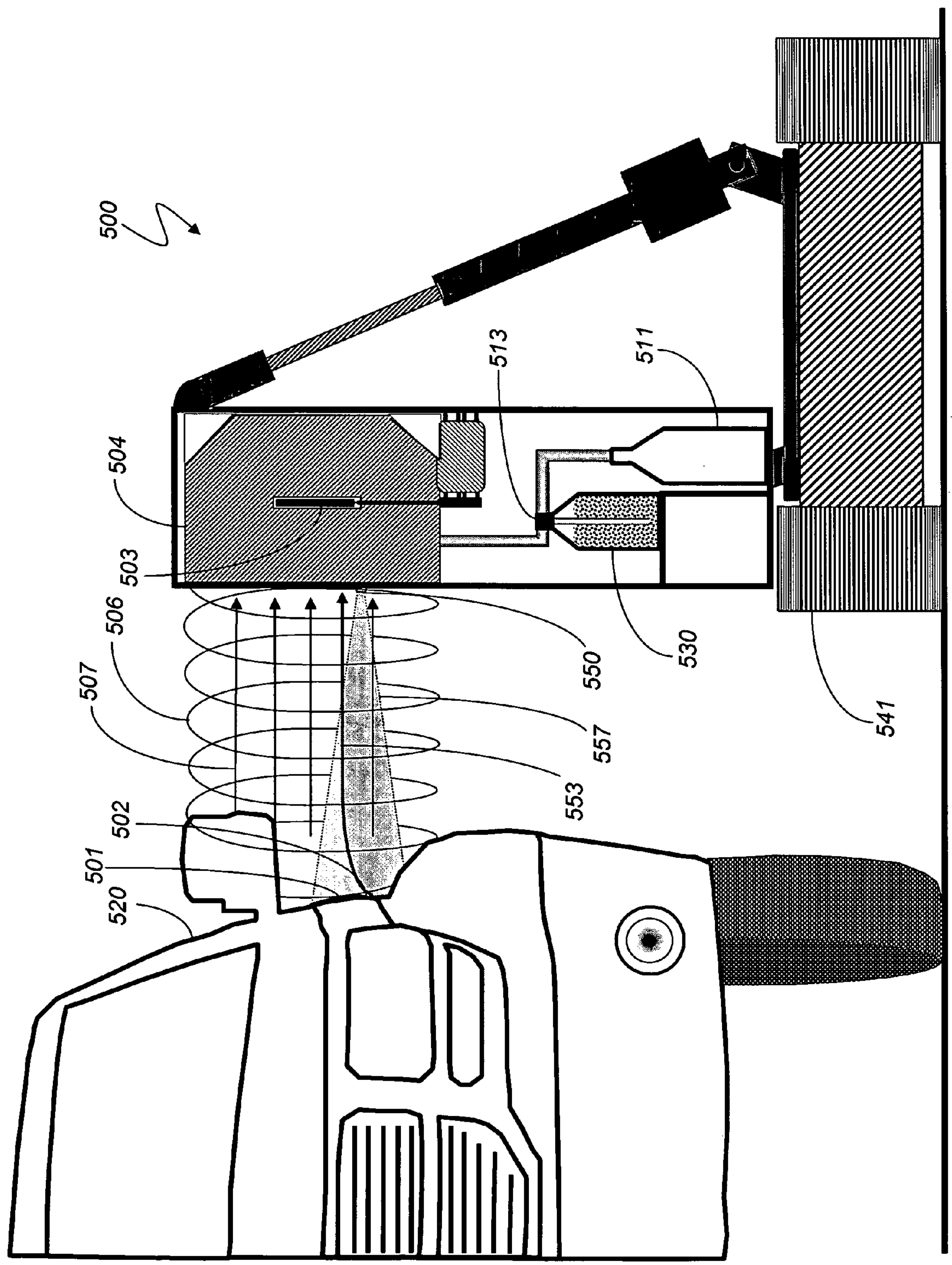
FIG. 6 is a schematic diagram showing an application of the method for non-contact collection of trace particles of explosives or narcotics from a target surface when the trace sample collection system is moving on a tracked vehicle and the target object is static, according to an embodiment of the system described herein.

FIG. 6 shows a system 500 having another configuration that employs the non-contact collection of trace particles of explosives or narcotics from a target surface according to an embodiment of the system described herein. In this configuration a target object surface 501 is static and a trace sample collection system 504 is moving. The example shown is for a static vehicle 520 with the trace sample collection system 504 on a moving robotic platform, but a similar configuration with a different motion mechanism may be used for a human portal to inspect for trace particles of explosives or narcotics on clothing. The trace sample collection system 504 based on the vortex attractor design is shown disposed to the side of the vehicle 520 with the target surface 501 as the door handle and door seam of the vehicle 520. The vortex attractor may use a single mechanism, preferably an impeller, for producing both the outwardly blowing and spinning gas flow 506 and the inwardly flowing gas and air flow 507. In the example shown in the figure, particles 553 are being released from a particle source 502 on the vehicle door. An aerosol nozzle 550 disposed within the inwardly flowing gas and air flow 507 may blow an aerosol jet 557 towards the target surface 501. The sample collecting media 503 may be disposed within the inwardly flowing gas and air flow 507, which may also entrain the released trace particles of explosives or narcotics 553. In the example shown, the aerosol particles may be supplied from a reservoir 530. The gas for mixing with the aerosol particles may be supplied from a reservoir 511 and combine with the aerosol particles in a mixing chamber and valve 513.

The motion for the robotic platform carrying the trace sample collection system 504 may be provided by a tracked drive system 541.

The system described herein may incorporate any combination of the embodiments discussed herein as well as other features, such as features described in commonly assigned copending applications and/or issued U.S. patents, such as U.S. Application No. 60/708,017, filed Oct. 25, 2005, U.S. Pat. No. 6,861,646, U.S. Pat. No. 6,870,155, and U.S. Pat. No. 6,888,128, which are all incorporated herein by reference, and/or other patents or patent applications incorporated herein by reference.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A method for non-contact collection of trace particles of explosives or narcotics from a target surface, comprising:

releasing said trace particles from the target surface;

providing transport for said trace particles that includes a vortex directed outwardly towards said target surface, wherein said vortex projects from an exit orifice for an outwardly blowing and spinning gas flow that is concentric with an inwardly flowing gas and air flow;

collecting said trace particles from said inwardly flowing gas and air flow, wherein a relative velocity across the line-of-sight between said target surface and said exit orifice for said outwardly blowing and spinning gas flow is greater than 15 centimeters per second.

2. The method for non-contact collection of trace particles according to claim 1, wherein said releasing said particles includes use of a jet that is at least one of: a jet of gas and an aerosol jet.

3. The method for non-contact collection of trace particles according to claim 2, wherein said jet is directed towards the area on said target surface that is within the portion of said vortex that is the inwardly flowing gas and air flow.

4. The method for non-contact collection of trace particles according to claim 2, wherein said jet blows said trace particles into said inwardly flowing gas and air flow.

5. The method for non-contact collection of trace particles according to claim 1, wherein said outwardly blowing and spinning gas flow rotates about the axis defined by the inwardly flowing gas and air flow.

6. The method for non-contact collection of trace particles according to claim 5, wherein said gas is at least one of: air, carbon dioxide, nitrogen, and argon.

7. The method for non-contact collection of trace particles according to claim 5, wherein a temperature of said gas of the outwardly blowing and spinning gas flow is at or above ambient temperature.

8. The method for non-contact collection of trace particles according to claim 5, wherein the outwardly blowing and spinning gas flow contains additive chemicals that enhance detection performance.

9. The method for non-contact collection of trace particles according to claim 5, wherein said outwardly blowing and spinning gas flow and said inwardly flowing gas and air flow are provided by a unified system.

10. The method for non-contact collection of trace particles according to claim 9, wherein the unified system is a vortex attractor.

11. The method for non-contact collection of trace particles according to claim 1, wherein said inwardly flowing gas and air flow forms a partial vacuum of sufficient strength to provide a force directed radially inwards towards the axis defined by the center of the inwardly flowing gas and air flow, said force being substantially equal to the centrifugal force directed radially outwards due to the rotation of the outwardly blowing and spinning gas flow.

12. The method for non-contact collection of trace particles according to claim 1, wherein said providing said outwardly blowing and spinning gas of said vortex is by at least one of: a gas pump, a fan, an impeller, a blower, an air knife, and a pressurized air supply.

13. The method for non-contact collection of trace particles according to claim 1, wherein said providing said inwardly flowing gas and air of said vortex is by at least one of: a vacuum pump, a fan, an impeller, and a Venturi vacuum generator.

14. The method for non-contact collection of trace particles according to claim 1, wherein said exit orifice for said outwardly blowing and spinning gas flow is greater than 3.75 centimeters in diameter.

15. The method for non-contact collection of trace particles according to claim 1, wherein said collecting said trace particles includes use of at least one of: a mesh filter, a woven three dimensional mesh, a filter made of filter materials, a surface that is chemically coated to enhance adhesion or adsorption, a vortex particle separator, an electrostatic particle collector, a particle impactor, and an engineered material with etched openings to pass gas and air but preferentially retain particles.

16. The method for non-contact collection of trace particles according to claim 1, wherein a plurality of systems for non-contact collection of trace particles are employed in order to increase the sampled area of target surface.

17. The method for non-contact collection of trace particles according to claim 1, wherein a plurality of systems for non-contact collection of trace particles are employed in order to balance suction forces on a lightweight target surface.

18. The method for non-contact collection of trace particles according to claim 1, wherein a plurality of systems for non-contact collection of trace particles are employed in order to decrease the time required to obtain said collection of trace particles.

19. A system for non-contact collection of trace particles of explosives or narcotics from a target surface, comprising:

a particle release component that releases the trace particles from the target surface;

a particle transport component that transports the trace particles from the target surface, wherein the particle transport component provides a vortex directed outwardly towards the target surface, wherein the vortex projects from an exit orifice for an outwardly blowing and spinning gas flow that is concentric with an inwardly flowing gas and air flow;

a particle collection component that collects the trace particles from the inwardly flowing gas and air flow, wherein a relative velocity across the line-of-sight between said target surface and said exit orifice for the outwardly blowing and spinning gas flow is greater than 15 centimeters per second.

20. The system for non-contact collection of trace particles according to claim 19, wherein particle release component includes a nozzle that outputs at least one of: a jet of gas and an aerosol jet.

21. The system for non-contact collection of trace particles according to claim 19, wherein the particle transport component includes a vortex sampling system.

22. The system for non-contact collection of trace particles according to claim 19, wherein the particle collection component includes at least one of: a mesh filter, a woven three dimensional mesh, a filter made of filter materials, an absorbent surface that may be chemically coated to enhance adhesion, a vortex particle separator, an electrostatic particle collector, a particle impactor, and an engineered material with etched openings to pass air but retain particles.

* * * * *